US00PP37185P2

(12) United States Plant Patent
Pounders

(10) Patent No.: US PP37,185 P2
(45) Date of Patent: Dec. 30, 2025

(54) ***LAGERSTROEMIA* PLANT NAMED '19-025'**

(50) Latin Name: ***Lagerstroemia indica* x *speciosa***
Varietal Denomination: 19-025

(71) Applicant: Capstone Plants, Inc., Grand Saline, TX (US)

(72) Inventor: Cecil T. Pounders, Decatur, AL (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 18/747,632

(22) Filed: Jun. 19, 2024

(51) Int. Cl.
*A01H 6/00* (2018.01)
*A01H 5/02* (2018.01)

(52) U.S. Cl.
USPC ..... Plt./252

(58) Field of Classification Search
USPC ..... Plt./252
CPC ..... A01H 6/00; A01H 5/02
See application file for complete search history.

*Primary Examiner* — Keith O. Robinson
(74) *Attorney, Agent, or Firm* — Weatherly IP Solutions, LLC; James Weatherly; Karen Bechtold

(57) ABSTRACT

A new cultivar of *Lagerstroemia* plant named '19-025' distinguished by large dark purple foliage, sterile lavender flowers, cold hardiness, and a compact growth habit, is disclosed.

2 Drawing Sheets

Genus and species: *Lagerstroemia indica* x *speciosa.*
Variety denomination: '19-025'.

BACKGROUND

The present disclosure relates to a new and distinct cultivar of *Lagerstroemia* plant, commonly known as Tropical Crape Myrtle, a shrub that is grown for use as an ornamental landscape and container plant. The new variety is known botanically as *Lagerstroemia indica* x *speciosa* and will be referred to hereinafter by the cultivar name '19-025'.

'19-025' originated and was selected from a *Lagerstroemia* breeding program which was started in 2018. '19-025' was selected by the inventor in 2020 as a seedling from a cross of the female parent variety *Lagerstroemia* 'Big Pink' (unpatented) after a controlled cross pollination by male *Lagerstroemia* variety 'Ebony Flame' (unpatented). '19-025' was selected for its large dark purple foliage, sterile lavender flowers, cold hardiness and a compact growth habit.

'19-025' was first asexually propagated under the control of the inventors in 2020 in a greenhouse in Grand Saline, Texas using softwood cuttings. The inventors have confirmed that '19-025' is stable and reproduces true to type in successive generations of asexual reproduction.

SUMMARY

The following traits have been repeatedly observed and represent the distinguishing characteristics of '19-025'. '19-025' has not been tested under all possible conditions and phenotypic differences may be observed with variations in environmental, climatic, and cultural conditions, without however, any variance in genotype.

1. Large dark purple foliage;
2. Sterile lavender flowers;
3. Cold hardiness; and 4. A compact growth habit.

DESCRIPTION OF THE PHOTOGRAPHS

The accompanying color photographs illustrate the overall appearance of the new *Lagerstroemia* cultivar '19-025' showing the colors as true as it is reasonably possible to obtain in colored reproductions of this type. Photographs were taken of a 10-month old plant in 2024 in Grand Saline, Texas. Colors in the photographs may differ from the color values cited in the detailed botanical description, which more accurately describes the actual colors of the new variety '19-025'.

DESCRIPTION OF THE NEW VARIETY

Figure 1:
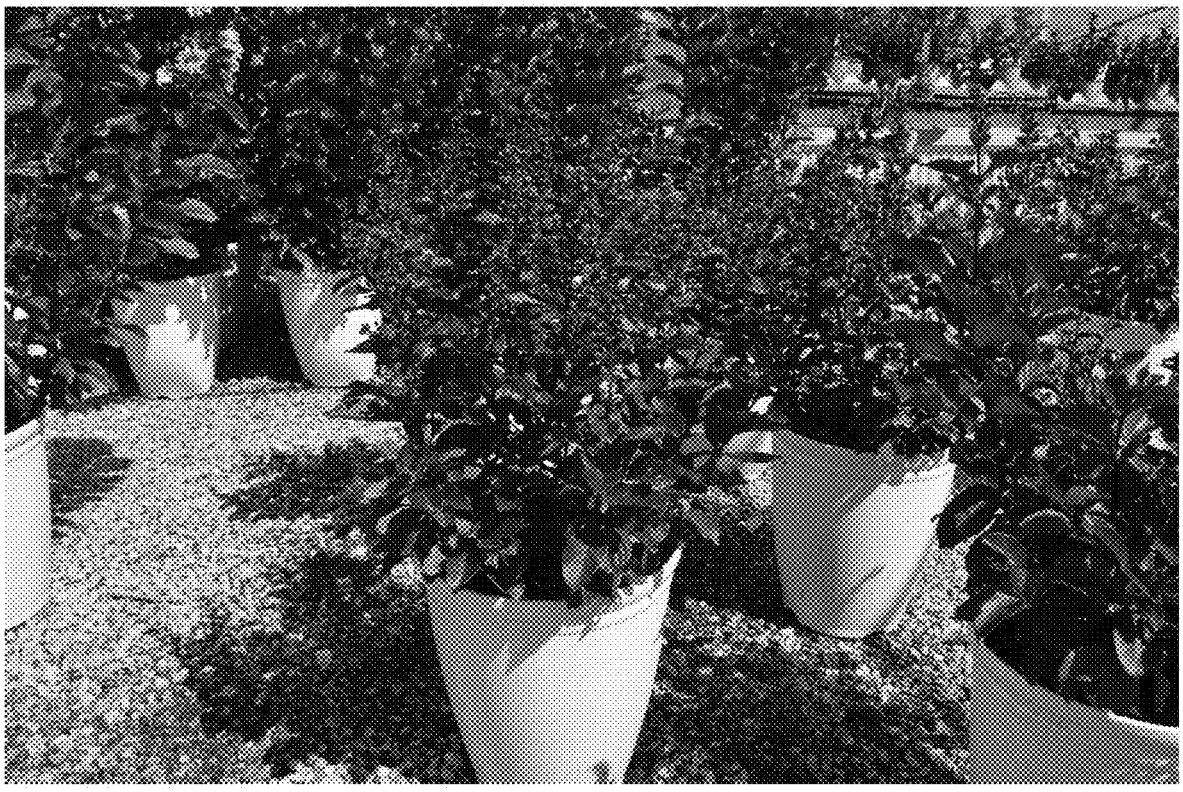
FIG. 1 depicts a view of the entire plant of '19-025'.
Figure 2:
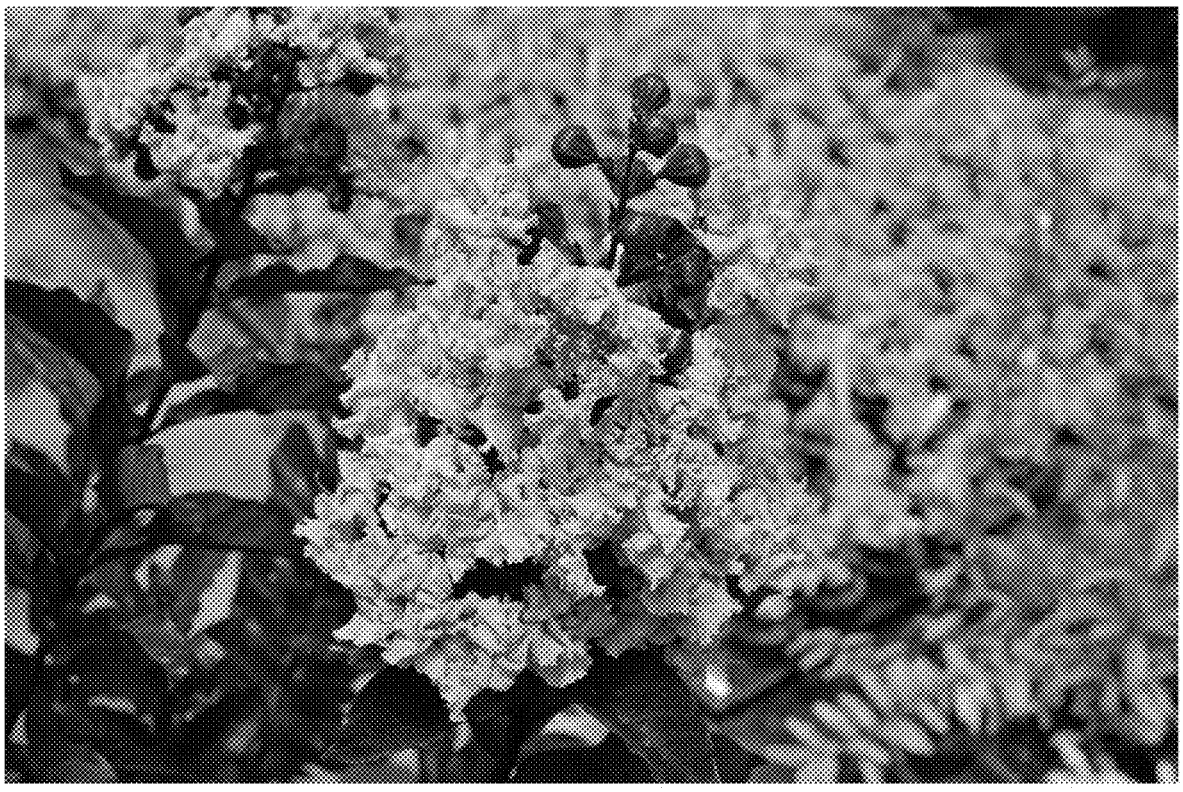
FIG. 2 depicts a close-up view of the inflorescence and flowers of '19-025'.

The following detailed descriptions set forth the distinctive characteristics of '19-025'. Observations, measurements, values, and comparisons were collected in Spring 2024 in Grand Saline, Texas from fifteen-month old plants which were growing outdoors in full sun in a 2-gallon container. Color determinations were made in accordance with The 2007 Royal Horticultural Society Colour Chart from London England, except where general color terms of ordinary dictionary significance are used.

Classification:
*Family.*—Lythraceae.
*Genus.*—*Lagerstroemia.*
*Species.*—*Indica* x *speciosa.*
*Common name.*—Tropical Crape Myrtle.

Parentage:
*Female parent.*—*Lagerstroemia speciosa* 'Big Pink' (unpatented).
*Male parent.*—*Lagerstroemia indica* 'Ebony Flame' (unpatented).

Plant:
*Type*.—Annual in most zones.
*Vigor*.—Vigorous.
*Habit*.—Upright.
*Plant dimensions* (*after* 1 *year*).—4'×20".
*Plant dimensions* (*mature*).—15'×12'.
*Hardiness USDA zone*.—This clone is root hardy where the ground doesn't freeze — zone 8B and stem hardy without freezing temperatures — zone 9B.
*Root system type*.—Fibrous.
*Root color*.—RHS 18C.
*Recommended soil and growing conditions*.—Plant in a good mixture of sandy loam soil that drains pretty well.
*Recommended light conditions* (*sun, shade*).—Full sun or part shade.
*Crop time*.—50ct liner transplant to 2 gallon: 4-5 months.
*Seasonal interest*.—Spring and Summer.
*What method used for propagation*.—Asexual, softwood cuttings.
*Time to initiate roots*.—10 to 14 days.
*Heat and humidity tolerance*.—Good heat and humidity tolerance that prefers a more tropical environment rather than a hot dry climate.

Basal stems:
*Shape*.—Round.
*Diameter*.—1.3 cm.
*Bark color*.—199B.
*Texture*.—Slightly coarse or textured.

Branches:
*Branching habit*.—Well branched, upright.
*Internode length*.—1.0 cm to 3.0 cm.
*Stem diameter*.—0.5 cm.
*Stem length*.—40 cm to 80 cm.
*Stem shape*.—Round.
*Stem surface*.—Slightly coarse and textured.
*Stem color* (*juvenile*).—RHS 187A.
*Stem color* (*mature*).—RHS 199A.
*Stem strength*.—Firm.

Leaves:
*Type, arrangement*.—Deciduous, simple, alternate.
*Attachment*.—Petiolate.
*Leaf aspect*.—Upward facing towards apex.
*Leaf shape*.—Ovate.
*Leaf base*.—Acute.
*Leaf apex*.—Obtuse.
*Leaf venation*.—Pinnate.
*Vein color* (*upper surface*).—RHS 187A.
*Vein color* (*lower surface*).—RHS 187B.
*Vein aspect* (*raised or depressed*).—Raised.
*Leaf surface* (*upper*).—Smooth.
*Leaf surface* (*lower*).—Veins on back providing slight texture.
*Glossiness of leaf blade*.—Medium.
*Leaf dimensions* (*current growth*).—3¼" long×1½" wide.
*Leaf dimensions* (*previous year growth*).—4" long×1¾" wide.
*Leaf color* (*upper*).—RHS 203C.
*Leaf color* (*lower*).—RHS N200A.
*Leaf margin*.—Entire.

Petiole:
*Dimensions*.—4.0 mm×3.0 mm.
*Shape*.—Round.
*Surface*.—Smooth.
*Color*.—RHS 187A.

Peduncle:
*Shape*.—Elongated cylinder.
*Dimensions*.—9.0 mm long×1.0 mm wide.
*Surface*.—Smooth.
*Color* RHS 187A.

Inflorescence:
*Type*.—Panicle.
*Width and length*.—14.0 cm×7 cm to 28 cm×11 cm.
*Thyrse*.—Approximately 36, triangular shaped, and approximately 1.9 cm to 3.8 cm long.

Pedicels:
*Shape*.—Elongated cylindrical.
*Length*.—4.0 mm.
*Diameter*.—1.0 mm.
*Texture*.—Smooth.
*Color*.—RHS 200B.

Calyx:
*Shape*.—Campanulate.
*Height*.—1.0 cm.
*Diameter*.—2.4 cm.

Sepals:
*Quantity*.—6.
*Shape*.—Acutely triangular.
*Length*.—5.0 mm.
*Width at base*.—4.0 mm.
*Margin*.—Entire.
*Surface* (*adaxial surface*).—Smooth.
*Surface* (*abaxial surface*).—Smooth.

Flowers:
*Quantity per plant*.—276.
*Shape*.—Obovate.
*Fragrance*.—Little to none.
*Length*.—4.5 cm.
*Width*.—2.5 cm.
*Time from bud set to full flower*.—Approximately 3 weeks.

Bud:
*Shape*.—Oval.
*Dimensions*.—11 mm×10 mm.
*Surface*.—Smooth with very fine hairs.
*Color*.—RHS 187B.

Petals:
*Quantity*.—6.
*Arrangement*.—Rotate.
*Shape*.—Obovate.
*Length*.—2.2 cm.
*Width*.—2.0 cm.
*Apex*.—Round.
*Base*.—Reniform.
*Margin*.—Undulate.
*Color* (*both surfaces*).—RHS 79D.

Reproductive organs:
*Stamens, filaments*.—Quantity: 72. Arrangement: Upright in a cluster. Length: 1.0 mm. Diameter: 9.0 mm. Color: RHS 11C. Conspicuousness of stamen: Conspicuous.
*Anthers*.—Shape: Saddle shaped. Length: 9.0 mm. Width: 1.0 mm. Color: 200D.
*Pollen*.—Amount: Ample. Color: RHS 13A.

*Pistil*.—Quantity: 1. Dimensions: 9.0 mm in length, 1.0 mm in diameter.

*Stigma*.—Shape: Club shaped. Length: 1 mm. Diameter: 22 mm. Color: 142C.

*Ovary*.—Shape: Globular. Length: 2.0 mm. Diameter: 3.0 mm. Color: RHS 5D.

Seed: None observed to date.

Pest susceptibility: Slightly susceptible to aphids (*Aphis gossypii*) and occasionally to whitefly (*Trialeurodes vaporariorum*).

Disease susceptibility: Slight incidence of *Erysiphe lagerstroemiae*; Improved resistance to prevalent crape myrtle diseases.

Heat, humidity and drought tolerance: Very well adapted to heat, humidity and drought conditions.

COMPARISON WITH PARENTAL LINES AND KNOWN VARIETY

'19-025' is distinguished from its female parent variety *Lagerstroemia* 'Big Pink' in that '19-025' has smaller foliage than 'Big Pink' with sterile lavender flowers while Big Pink has pink fertile flowers. '19-025' has been shown to be cold tolerant while 'Big Pink' is susceptible to cold temperatures.

'19-025' is distinguished from it male patent variety *Lagerstroemia* 'Ebony Flame' in that Ebony Flame has smaller leaves, a more open growth habit than '19-025'. 'Ebony Flame' has red fertile flowers while '19-025' has sterile lavender flowers. 'Ebony Flame' is also much more cold hardy than '19-025'.

'19-025' is distinguished from commercial *Lagerstroemia* variety 'Delta Eclipse' (unpatented). '19-025' has longer and wider leaves than 'Delta Eclipse'. The leaves of '19-025' are more waxy in appearance and '19-025' has a higher growth rate compared to 'Delta Eclipse'.

I claim:

1. A new and distinct cultivar of *Lagerstroemia* Plant Named '19-025' as described and illustrated herein.

* * * * *